(12) United States Patent
Magno et al.

(10) Patent No.: US 11,992,256 B2
(45) Date of Patent: May 28, 2024

(54) ELECTROSURGICAL ATTACHMENT DEVICE

(71) Applicant: GYRUS ACMI, INC., Southborough, MA (US)

(72) Inventors: Joey Magno, Dudley, MA (US); Joel Andrew Willhite, Memphis, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 520 days.

(21) Appl. No.: 17/186,115

(22) Filed: Feb. 26, 2021

(65) Prior Publication Data

US 2021/0267660 A1 Sep. 2, 2021

Related U.S. Application Data

(60) Provisional application No. 62/982,821, filed on Feb. 28, 2020.

(51) Int. Cl.
*A61B 18/14* (2006.01)
*A61B 18/00* (2006.01)

(52) U.S. Cl.
CPC .... *A61B 18/14* (2013.01); *A61B 2018/00136* (2013.01); *A61B 2018/00178* (2013.01);
(Continued)

(58) Field of Classification Search
CPC .......... A61B 18/14; A61B 2018/00136; A61B 2018/00178; A61B 2018/00595; A61B 2018/00982; A61B 18/1485; A61B 1/00101; A61B 1/00135; A61B 1/227; A61B 1/233; A61B 2018/00327
(Continued)

(56) References Cited

U.S. PATENT DOCUMENTS 6,071,233 A 6/2000 Ishikawa et al.
6,086,583 A * 7/2000 Ouchi ................ A61B 18/1492
604/35
(Continued)

FOREIGN PATENT DOCUMENTS

EP 0637436 A1 2/1995
EP 1639936 A1 3/2006
(Continued)

OTHER PUBLICATIONS

"European Application Serial No. 21153679.2, Extended European Search Report dated Jun. 24, 2021", 6 pgs.
(Continued)

*Primary Examiner* — Michael F Peffley
(74) *Attorney, Agent, or Firm* — Schwegman Lundberg & Woessner, P.A.

(57) ABSTRACT

An electrosurgical device is provided. The electrosurgical device can include an elongated member configured to be attached to an elongated shaft of an endoscope, the elongated member including a distal portion that, when axially extended beyond a distal end of the shaft, bends toward a longitudinal axis of the shaft. The electrosurgical device can include an electrode exposed at the distal portion of the elongated member. The electrosurgical device can include an electrical interconnect coupling the electrode to an electrosurgical energy connection at a proximal portion of the elongated member.

26 Claims, 8 Drawing Sheets

(52) U.S. Cl.
CPC ............... *A61B 2018/00595* (2013.01); *A61B 2018/00982* (2013.01)

(58) Field of Classification Search
USPC .......................................................... 606/46
See application file for complete search history.

(56) References Cited

U.S. PATENT DOCUMENTS

| | | | |
|---|---|---|---|
| 6,352,503 | B1 | 3/2002 | Matsui et al. |
| 7,997,278 | B2 | 8/2011 | Utley et al. |
| 8,052,683 | B2 * | 11/2011 | Podmore ............... A61B 90/36 606/41 |
| 8,715,281 | B2 * | 5/2014 | Barlow .............. A61B 18/1492 606/113 |
| 9,931,019 | B2 | 4/2018 | Herrmann et al. |
| 10,098,524 | B2 | 10/2018 | Cheng et al. |
| 11,051,682 | B2 | 7/2021 | Molnar |
| 2002/0177847 | A1 | 11/2002 | Long |
| 2006/0050143 | A1 | 3/2006 | Ouchi |
| 2006/0069304 | A1 | 3/2006 | Takemoto et al. |
| 2006/0270900 | A1 * | 11/2006 | Chin ...................... A61B 1/313 606/1 |
| 2008/0027280 | A1 | 1/2008 | Fengler et al. |
| 2008/0277853 | A1 | 11/2008 | Menn |
| 2016/0157697 | A1 | 6/2016 | Arai et al. |
| 2016/0206178 | A1 | 7/2016 | Lau |
| 2017/0049302 | A1 | 2/2017 | Isoda |
| 2017/0127917 | A1 | 5/2017 | Cheng et al. |
| 2018/0250496 | A1 | 9/2018 | Melsheimer et al. |
| 2019/0167075 | A1 | 6/2019 | Fischer et al. |
| 2021/0186314 | A1 | 6/2021 | Hwang et al. |
| 2021/0228062 | A1 | 7/2021 | Edwards |
| 2021/0267436 | A1 | 9/2021 | Yamashita |
| 2021/0290045 | A1 | 9/2021 | Takeuchi et al. |
| 2022/0322916 | A1 | 10/2022 | Bagwell et al. |

FOREIGN PATENT DOCUMENTS

| | | | |
|---|---|---|---|
| WO | WO-9510981 A1 | 4/1995 | |
| WO | WO-0195810 A2 * | 12/2001 | ..... A61B 17/320725 |
| WO | WO-0195810 A2 | 12/2001 | |

OTHER PUBLICATIONS

"European Application Serial No. 21159790.1, Extended European Search Report dated Jul. 13, 2021", 7 pgs.

"InstaClear Product Guide", Olympus America Inc., (2017), 2 pgs.

"Visera 4K UHD—CH-S400—4K Camera Head", Olympus America, [Online]. Retrieved from the Internet: < URL:, (Accessed Feb. 3, 2020), 2 pgs.

"Visera 4K UHD—Ultra Telescopy", Olympus America, [Online]. Retrieved from the Internet: <URL: https://medical.olympusamerica.com/products/VISERA-4K-UHD-System>, (Accessed Feb. 3, 2020), 2 pgs.

"Visera 4K UHD System", Olympus America, [Online]. Retrieved from the Internet: <URL: https://medical.olympusamerica.com/products/VISERA-4K-UHD-System#ultra_high_definition>, (Accessed Feb. 3, 2020), 5 pgs.

"U.S. Appl. No. 17/149,692, Examiner Interview Summary dated May 30, 2023", 2 pgs.

"U.S. Appl. No. 17/149,692, Final Office Action dated Sep. 27, 2023", 16 pgs.

"U.S. Appl. No. 17/149,692, Non Final Office Action dated Mar. 1, 2023", 15 pgs.

"U.S. Appl. No. 17/149,692, Response filed May 25, 2023 to Non Final Office Action dated Mar. 1, 2023", 10 pgs.

"European Application Serial No. 21153679.2, Response Filed Jan. 21, 2022 to Extended European Search Report dated Jun. 24, 2021", 7 pgs.

"European Application Serial No. 21159790.1, Response filed Feb. 26, 2022 to Extended European Search Report dated Jul. 13, 2021", 34 pgs.

"U.S. Appl. No. 17/149,692, Advisory Action dated Dec. 13, 2023", 3 pgs.

"U.S. Appl. No. 17/149,692, Response filed Nov. 16, 2023 to Final Office Action dated Sep. 27, 2023", 12 pgs.

* cited by examiner

```
┌─────────────────────────────────────────┐
│     PROVIDE ATTACHABLE AND DETACHABLE   │
│      ELONGATED MEMBER THAT, WHEN AXIALLY│
1002 ─│ EXTENDED BYOND A DISTAL END OF A SHAFT OF AN│
│      ENDOSCOPE, BENDS TOWARDS A LONGITUDINAL│
│              AXIS OF THE SHAFT          │
└─────────────────────────────────────────┘
                    │
┌─────────────────────────────────────────┐
1004 ─│  CAUSE ELECTRICITY TO FLOW AN ELECTRODE OF │
│              THE ELONGATED MEMBER       │
└─────────────────────────────────────────┘
```

*FIG. 10*

ELECTROSURGICAL ATTACHMENT DEVICE

CROSS-REFERENCE TO RELATED APPLICATION

This application claims the benefit of priority to U.S. Provisional Application No. 62/982,821 filed on Feb. 28, 2020, the content of which is incorporated herein in its entirety.

FIELD

This document relates to attachments for electrosurgical medical devices. The attachment can provide cautery function to a device that would not otherwise have the cautery function.

BACKGROUND

Traditionally, sinus surgeons hold an endoscope in a dedicated hand ("scope hand") and exchange instruments of various forms and functions, such as cautery, with the other hand ("instrument hand"). These instrument exchanges can be time consuming and inconvenient. The instrument exchange can be particularly important when managing bleeding, such as when dissecting or resecting instruments are exchanged for a cauterizing instrument.

SUMMARY

These teachings can help overcome one or more of the problems discussed in the Background or elsewhere, such as by providing an endoscope with an electrosurgical device attachment that provides a cautery function.

For example, an electrosurgical device can include an elongated member configured to be attached to an elongated shaft of an endoscope. The elongated member can include a distal portion that, when axially extended beyond a distal end of the shaft, bends toward a longitudinal axis of the shaft. The electrosurgical device can include an electrode exposed at the distal portion of the elongated member. The electrosurgical device can include an electrical interconnect coupling the electrode to an electrosurgical energy connection at a proximal portion of the elongated member.

At least a portion of the elongated member can be situated at least partially around the shaft. The electrosurgical device can be an electrocautery device. The elongated member can include a transparent or translucent distal portion. The elongated member can be configured to accommodate a variety of shaft widths of the shaft, the shaft width perpendicular to the longitudinal axis of the shaft. The elongated member can include a gap extending from a distal portion to a proximal portion thereof to accommodate the variety of shaft widths.

The electrosurgical device can include a trigger at a proximal portion of the elongated member for actuating, by a user, an extension or retraction of the elongated member with respect to the shaft. The elongated member can be keyed to inhibit rotation of the elongated member about a longitudinal axis of the elongated member. The electrosurgical device can include a male or female connection feature configured to mate with a female or male connection feature of the endoscope.

The electrode can be a first electrode and the electrical interconnect can be a first electrical interconnect. The electrosurgical device can include a second electrode exposed at a distal portion of the elongated member. The electrosurgical device can include a second electrical interconnect coupling the second electrode to another electrosurgical energy connection at the proximal portion of the elongated member. The first and second electrodes can be physically separated.

These teachings can provide an electrosurgical system. The electrosurgical system can include an endoscope and an electrosurgical device. The endoscope can include an elongated shaft. The endoscope can include an optical illumination carrier to provide light to a distal end of the shaft. The endoscope can include an optical carrier to provide light incident on the distal end of the shaft to a proximal portion of the endoscope. The electrosurgical device can include an elongated member configured to be attached to the shaft. The elongated member can include a distal portion that, when axially extended beyond a distal end of the shaft, bends toward a longitudinal axis of the shaft. The electrosurgical device can include an electrode on the elongated member and exposed at the distal portion of the elongated member. The electrosurgical device can include an electrical interconnect coupling the electrode to an electrosurgical energy connection at a proximal portion of the elongated member.

The shaft can be rigid compared to the distal portion of the elongated member. The elongated member can include a polymer material. The distal portion of the elongated member, when axially retracted toward a proximal end of the shaft, can move away from the longitudinal axis of the shaft. The elongated member can be configured to accommodate a variety of shaft widths, the shaft width perpendicular to a longitudinal axis of the shaft. The elongated member can include a gap extending from a distal portion to a proximal portion thereof to accommodate the variety of shaft widths.

The electrosurgical device can include an extension feature mechanically coupled to a proximal portion of the elongated member. The extension feature can include a finger control and at least one of (a) a cam follower, (b) a spring, or (c) lever. The elongated member can be keyed to inhibit rotation of the elongated member about a perimeter of the shaft. The distal portion of the elongated member can be transparent or translucent.

These teachings can provide a method of using an electrosurgical device. The method can include providing an elongated member. The elongated member can be attachable to and detachable from an elongated shaft of an endoscope. The elongated member can include an electrode exposed at a distal portion thereof. The elongated member, when axially extended beyond a distal end of the shaft, can bend toward a longitudinal axis of the shaft. The method can include causing electricity to flow through the electrode. The method can include axially extending the elongated member such that a portion of the electrode extends beyond a distal end of the shaft. The method can include axially retracting the elongated member such that a distal end of the elongated member moves away from the longitudinal axis of the shaft.

DETAILED DESCRIPTION

Some ear, nose, and throat (ENT) devices, such as an endoscope, can benefit from a cauterizing function to control bleeding, such as without having to remove the scope, introduce a cautery device to control bleeding, and re-introduce the scope. The bleeding, if not controlled, can negatively affect visibility using the ENT device. The ENT device can include a bipolar cautery function on a perimeter of a shaver blade cutting window or the cautery function can be a separate or independent device, such as a wand or bipolar forceps. The bipolar forceps can involve removal of the shaver from the surgical site before usage.

A bleeding tissue can at least partially block a view provided by the ENT device. A lens cleaner attachment can help clean the lens and improve the view. However, the cleaning attachment does not stop the bleeding. The cleaning device just cleans the lens of the ENT device.

It would be beneficial to reduce the number of steps or time it takes to perform an ENT procedure. The number of steps or time can be reduced by reducing instrument-swapping or other delays in controlling or stopping bleeding. It would also be beneficial to provide an improved view using the ENT device.

An electrosurgical device can be detachably coupled to a shaft of an endoscope. The combination of the electrosurgical device and endoscope can provide an electrosurgical system with endoscopic and cautery functions. The electrosurgical device can include an elongated member such as with one or more electrodes on, or at least partially in, the elongated member. The electrodes of the electrosurgical device can be exposed on a distal portion of the electrosurgical device. The electrosurgical device can be extended or retracted axially along the shaft of the endoscope. After extension, the distal portion of the elongated member can extend beyond a distal end of the endoscope shaft. A portion of the elongated member, including an exposed portion of the electrodes, can bend towards a longitudinal axis of the shaft. The electrode-carrying portion of the elongated member can be situated within a field of view of the endoscope, such as to permit viewing via the endoscope of cautery via the one or more electrodes.

The user of the electrosurgical device can electrically energize the electrodes to perform a cautery function. Since the elongated member is within the field of view, the user can be visually informed as to what is being cauterized, as it is being cauterized.

To extend the elongated member, the user can activate a trigger. The trigger can include a spring, lever, cam follower, or other extension or retraction device. The trigger, when activated, can cause the elongated member to translate axially such as along the shaft towards (and at least partially off) the distal end of the shaft. The trigger, when released, can cause the elongated member to retract axially along the shaft. The retraction can cause the elongated member to translate along the shaft such as towards a scope-to-camera attachment.

An endoscope can provide optical illumination and visualization, such as internal to a patient. An endoscope can include a slender and tubular instrument shaft, which can be rigid or flexible, depending upon the application. An endoscope can be used to look inside a patient. The procedure of viewing inside a patient body is called an endoscopy. The endoscope can be used to examine internal organs like a throat, sinus cavity, or esophagus. An endoscope can be specialized, such as to view a target organ. Such specialized endoscopes can be named after their target organ. For example, a sinuscope is specialized to provide a view of a sinus cavity, an otoscope is specialized to provide a view of an inner ear, a laryngoscope is specialized to provide a view of a larynx, a cystoscope is specialized to provide a view of the bladder, a nephroscope is specialized to view the kidney, a bronchoscope is specialized to view the bronchus, an arthroscope is specialized to view a joint, a colonoscope is specialized to view a colon, and a laparoscope is specialized to view an abdomen or pelvis.

The endoscope can be used to visually examine and diagnose. The endoscope can be used to assist in surgery or other medical procedures. This document explains, among other things, how to modify an endoscope to provide further surgical assistance, such as by providing an endoscope with an electrosurgical device that provides a cautery function.

An attachable and detachable coupling to the endoscope can provide flexibility to a user. An endoscope can be used in ENT and other types of surgeries, for example in arthroscopy and laparoscopy, among others. Having the electrosurgical device integrally formed with the endoscope can narrow down use and application of the endoscope. However, providing an attachable and detachable electrosurgical attachment can increase the number of applications of the endoscope. Further, the attachable and detachable electrosurgical attachment provides a user an option to add electrosurgical functionality to a wide variety of endoscopes, without having to purchase a new endoscope. Endoscopes can have different view angles, and a variety of endoscopes can be helpful to achieve the proper view angle in a surgery. Integrally forming a cautery function into each endoscope can be cost prohibitive.

Figure 1:
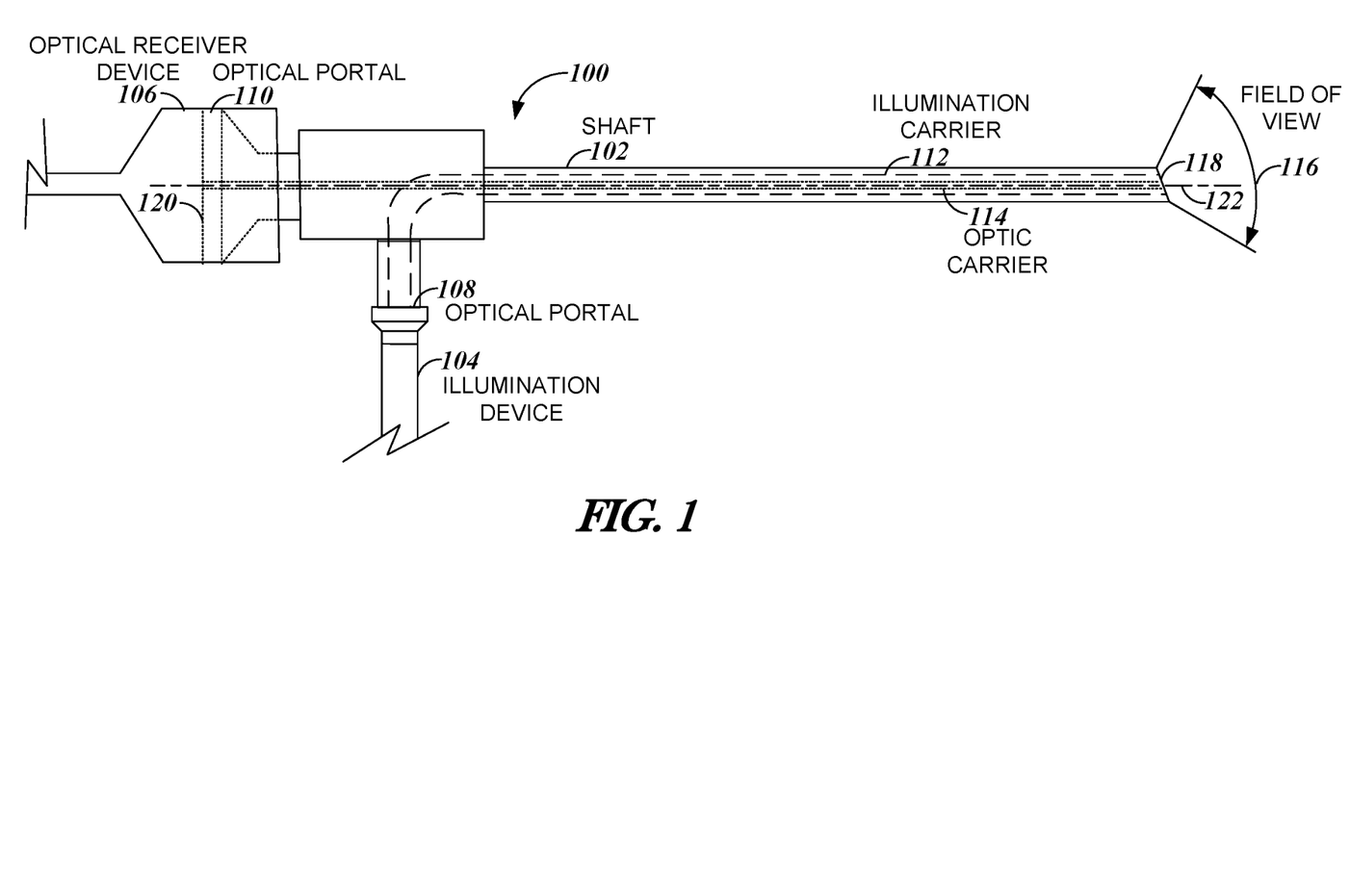
FIG. 1 illustrates an example of an endoscope system.

FIG. 1 illustrates an example of an endoscope system. The endoscope system can include an endoscope 100, an optical illumination device 104, and an optional optical receiver device 106. The optical illumination device 104 can convert an electrical signal to an optical signal. The optical illumination device 104 can provide the optical signal to an optic carrier 114 of the endoscope 100. The optical illumination device 104 can include or be coupled to an optical emitter, such as a laser, light emitting diode (LED), or the like.

The optical receiver device 106 can convert an optical signal carried by the optic carrier 114 into an electrical signal. The optical receiver device 106 can include a charge coupled device (CCD), a fiber optic receiver, or the like. An optical portal 110 can include a lens such as can help magnify the signal. A user can then view what is in a field of view 116 of the endoscope 100 through the lens. The field of view angle can vary from about 0° to about 70°. When included, the optical receiver device 106 can provide electrical signals that can be converted to image pixel values and provided for viewing such as on a display device.

The endoscope 100 can include an optical portal 108 such as to receive optical illumination from the illumination device 104. The optical portal 108 can include an illumination carrier 112 extending thereto. The illumination carrier 112 can communicate illumination light from the illumination device 104 to a distal end 118 of the endoscope 100. The illumination light can illuminate an object in the field of view 116. The illumination carrier 112 can include one or more optical fibers, mirrors, lenses, reflective surfaces, or the like, such as along a path that guides the light to the distal end 118.

The endoscope 100 can include another optical portal 110. The optic carrier 114 can carry incident light from within the field of view 116 to a proximal end 120 of the endoscope 100. The optic carrier 114 can include one or more optic fibers, mirrors, lenses, reflective surfaces, or the like.

A shaft 102 of the endoscope 100 can house the illumination carrier 112 and the optic carrier 114. The optic carrier 114 can be located within the illumination carrier 112 in the shaft 102. The shaft 102 can be rigid, flexible, or a combination thereof. For example, the shaft 102 can be rigid, entirely flexible, or can include some rigid and some flexible portions.

The shaft 102 can define a central longitudinal axis 122 extending a length thereof. The longitudinal axis 122 can extend from the proximal end 120 to the distal end 118.

Figure 2:
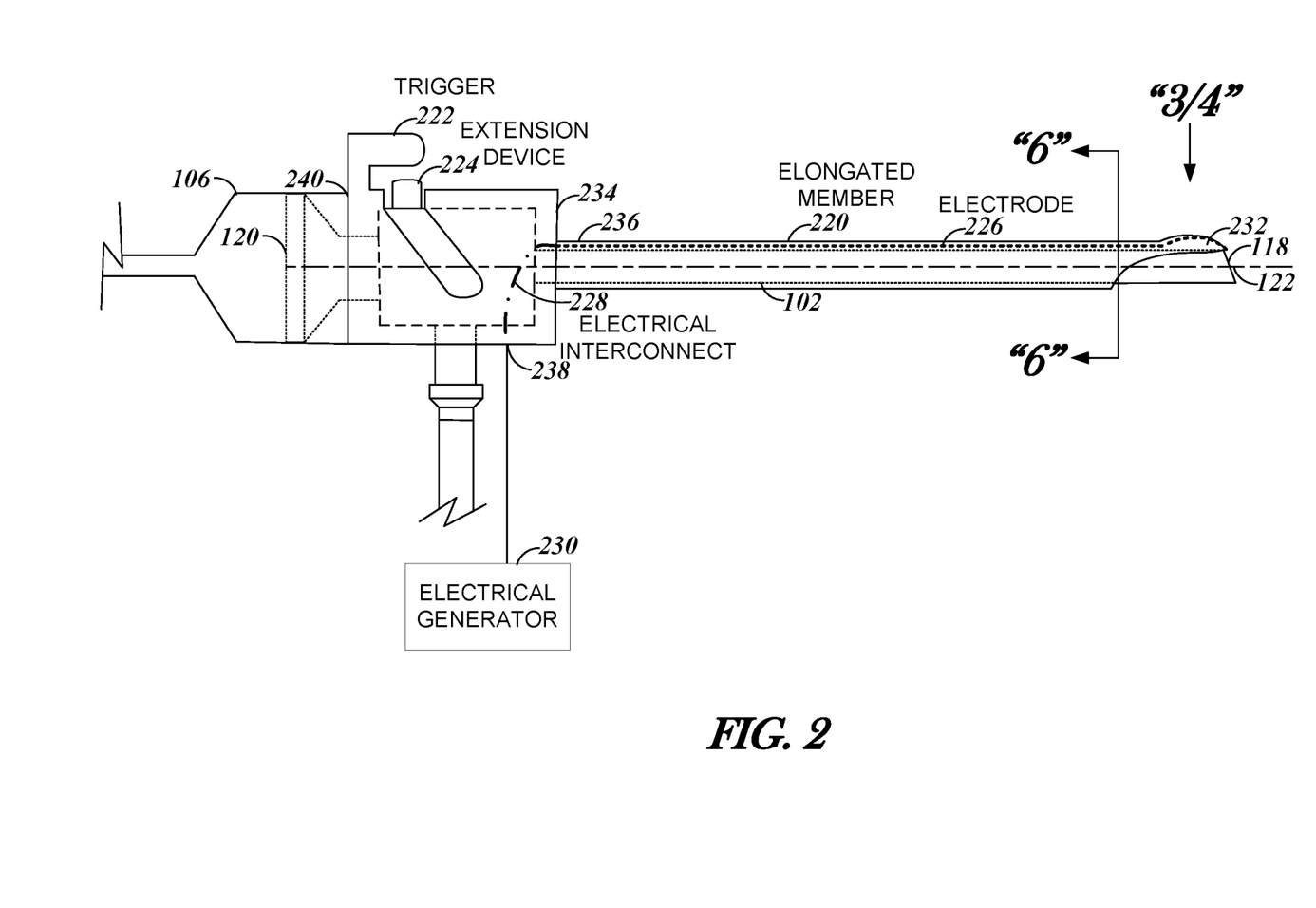
FIG. 2 illustrates an example of an endoscope system with a cautery function. The numbers in quotes with associated arrows indicate views provided in other FIGS.

FIG. 2 illustrates an example of an endoscope system with a cautery function. The arrows near numbers in quotes indicate views provided in other FIGS. The endoscope system includes the endoscope 100 (not labelled in FIG. 2 so as to not confuse the endoscope and the components that provide the cautery function), and an electrosurgical device coupled to the endoscope. The electrosurgical device can include an elongated member 220, a trigger 222, an extension device 224, one or more electrodes 226, and an electrical interconnect 228. The electrosurgical device can be electrically powered by an electrical generator 230.

The elongated member 220 can include the electrode 226 on or at least partially therein. The elongated member 220 can include a polymer material, such as a resin, rubber, plastic, elastomer, a combination thereof, or the like. The polymer can be molded. An example of a moldable polymer material is a United States Pharmacopeial Convention, Incorporated (USP) class IV ethylene tetrafluoroethylene (ETFE), polytetrafluoroethylene (PTFE), fluorinated ethylene propylene (FEP), or the like. The polymer can be flexible, pliable, stretchable, or a combination thereof. The polymer can include a shape memory characteristic such as can permit a distal portion 232 of the elongated member 220 to bend, such as when extended, such as to resume a shape provided upon its formation at manufacture. The elongated member 220 can include a distal portion 232 and a proximal portion 236.

The elongated member 220 can include a transparent or translucent distal portion 232. The distal portion 232 can include a material different from other portions of the elongated member 220. Such an elongated member 220 can allow a user to view the electrode 226 in the field of view 116. The transparent or translucent distal portion 232 can help the user see the bleeding or other obstruction to be cauterized.

The distal portion 232, when the elongated member 220 is in a retracted position (e.g., the position illustrated in FIG. 2), can be situated on the shaft 102. The proximal portion 236 can be mechanically coupled to a housing 234. The distal portion 232, when the elongated member 220 is in an extended position (e.g., the position illustrated in FIG. 5) can extend beyond the distal end 118 of the shaft 102. The distal portion 232, when the elongated member 220 is in an extended position, can bend toward the longitudinal axis 122, such as may result from a shape memory characteristic of its material of construction. The bending can cause the elongated member 220 to be within the field of view 116 (see FIG. 1).

The elongated member 220 can provide additional rigidity to the shaft 102 when coupled around the shaft 102. The elongated member 220 can be more rigid than the shaft 102 or less rigid than the shaft 102. That is, the flexural modulus of the shaft 102 can be greater or lesser than the flexural modulus of the elongated member 220. A higher flexural modulus corresponds to a stiffer or more rigid material.

The trigger 222 can be mechanically coupled to the housing 234. The trigger, when activated, can cause the extension device 224 to extend towards the distal end 118. The trigger 222 can be rotatable, pullable, pushable, or the like. The illustrated trigger 222 is rotatable. The trigger 222, when released, can cause the elongated member 220 to retract, such as to the position illustrated in FIG. 2.

The extension device 224 can include a pin, spring, lever, rod, cam follower, screw, a combination thereof, or the like. The extension device 224 can be mechanically coupled to the elongated member 220. The extension device 224, when extending (see FIG. 5) can cause the elongated member 220 to translate axially towards the distal end 118. The extension device 224, when retracting, can cause the elongated to translate axially towards the proximal end 120.

The housing 234 can be mechanically coupled to the optical receiver device 106. The housing 234 can accommodate the optical portal 108 and the illumination device 104. The housing 234 can provide protection for components situated at least partially therein, such as the extension device 224. The protection can be from forces incident thereon or from the external environment. The elongated member 220 can be mechanically coupled to the housing 234.

The one or more electrodes 226 are conductive elements. The electrode 226 conducts electricity from the electrical generator 230 to the distal portion 232. The voltage level of the electrode 226 can be sufficient to cauterize a structure proximate the distal portion 232. The electrode 226 can be made of gold, copper, silver, aluminum, zinc, nickel, brass, bronze, a combination thereof, or the like. The electrode 226 can be printed on the elongated member 220.

The electrical interconnect 228 can electrically couple the electrode 226 to an electrosurgical energy connection 238 at the proximal portion 236 of the elongated member 220. The electrical interconnect 228 can be electrically coupled between the electrode 226 and the electrical generator 230. The electrical interconnect 228 can provide electrical energy from the electrical generator 230 to the electrode 226.

The electrical generator 230 provides electrical power for use by the electrode 226. The electrical generator 230 can include a user-selectable range of voltage levels, current levels, power levels, frequencies, amplitudes, or the like. The electrical generator 230 can be used for a monopolar, bipolar, or other electrode configuration. The voltage level required for a monopolar cauterization can be higher than that for a bipolar cauterization.

The electrosurgical device can be mechanically coupled to the endoscope 100 such as at a connection interface 240. The optical receiver device 106 can include a male or female connection feature that is configured to mechanically mate with a female or male connection feature of the electrosurgical device, such as at the connection interface 240. The male or female connection feature of the connection interface 240 can include a tab, clip, magnet, detent, screw, thread, ball, slot, slit, hole, or the like configured to mate with a corresponding female or male connection feature of the connection interface 240.

Figure 3:
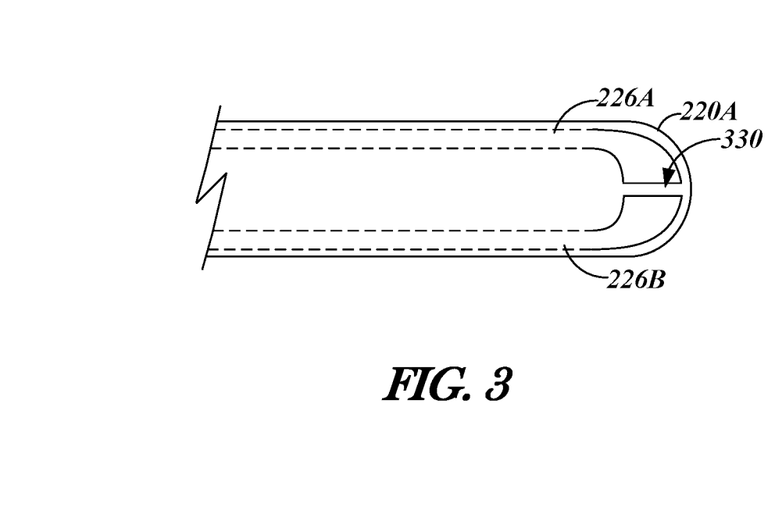
FIGS. 3 and 4 illustrate respective examples of electrode configurations.
Figure 4:
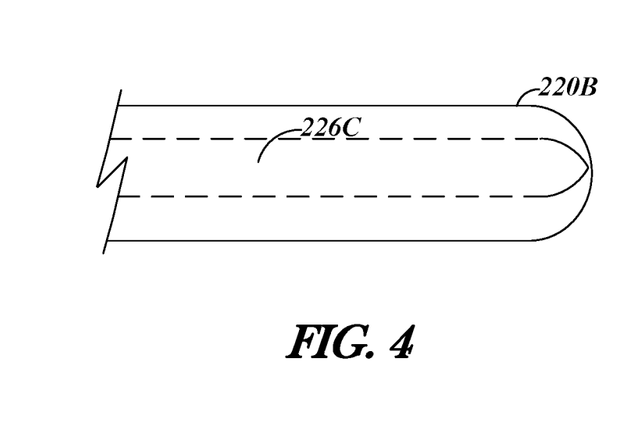

FIGS. 3 and 4 illustrate respective examples of electrode configurations. The electrode configuration in FIG. 3 includes a bipolar configuration. The electrode configuration in FIG. 4 includes a monopolar configuration. The view of FIGS. 3 and 4 is from the arrow labelled "3/4" in FIG. 2.

The bipolar configuration includes an elongated member 220A with multiple electrodes 226A, 226B. The electrodes 226A-226B can be on, or at least partially in, the elongated member 220A. The dashed lines can indicate locations where the electrodes 226A-226B are not exposed. The solid lines can indicate locations where the electrodes 226A-226B are exposed. The electrodes 226A-226B can be exposed at the distal portion 232 of the elongated member 220B. The electrodes 226A, 226B can be situated to define a gap 330 therebetween. Electrical energy can be provided by the electrical generator 230 to one of the electrodes 226A. The electrical energy can jump across the gap 330 to the other of the electrodes 226B and return to the electrical generator 230. A tissue near the gap 330 can be cauterized by the electrical energy jumping across the gap 330.

The monopolar configuration includes an elongated member 220B with a single electrode 226C. The electrode 226C can be on, or at least partially in, the elongated member 220C. The dashed lines can indicate locations where the electrode 226C is not exposed. The solid lines can indicate locations where the electrode 226C is exposed. The electrode 226C can be exposed at the distal portion 232 of the elongated member 220C. Electrical energy can be provided by the electrical generator 230 to the electrode 226C. The electrical energy can pass from the electrode 226C to proximate tissue, and through the tissue to a return pad. A tissue near the exposed portion of the electrode 226C can be cauterized by the electrical energy.

Since monopolar cautery has different energy requirements than bipolar cautery, an elongated member sufficient for bipolar cautery may not be sufficient for monopolar cautery. A material with a dielectric breakdown voltage characteristic sufficient for bipolar cautery may not be suitable for monopolar cautery. Some materials can break down and allow electrical energy to flow to the sheath 102, or other portion of the endoscope 100, or allow electrical energy to flow to a structure other than a structure that is to be cauterized. Thus, the material for the elongated member 220 can be an important consideration for proper operation of the electrosurgical device. Further, the thickness of the elongated member 220 can affect whether electricity will flow from the electrode 226 to the endoscope 100 or the patient. For greater voltages, a thicker elongated member 220 can help prevent electricity from flowing to the endoscope 100 or the patient at an undesired location.

A reference number with a letter suffix is a specific instance of a general component. For example, the electrode 226B is a specific instance of the one or more electrodes 226.

Figure 5:
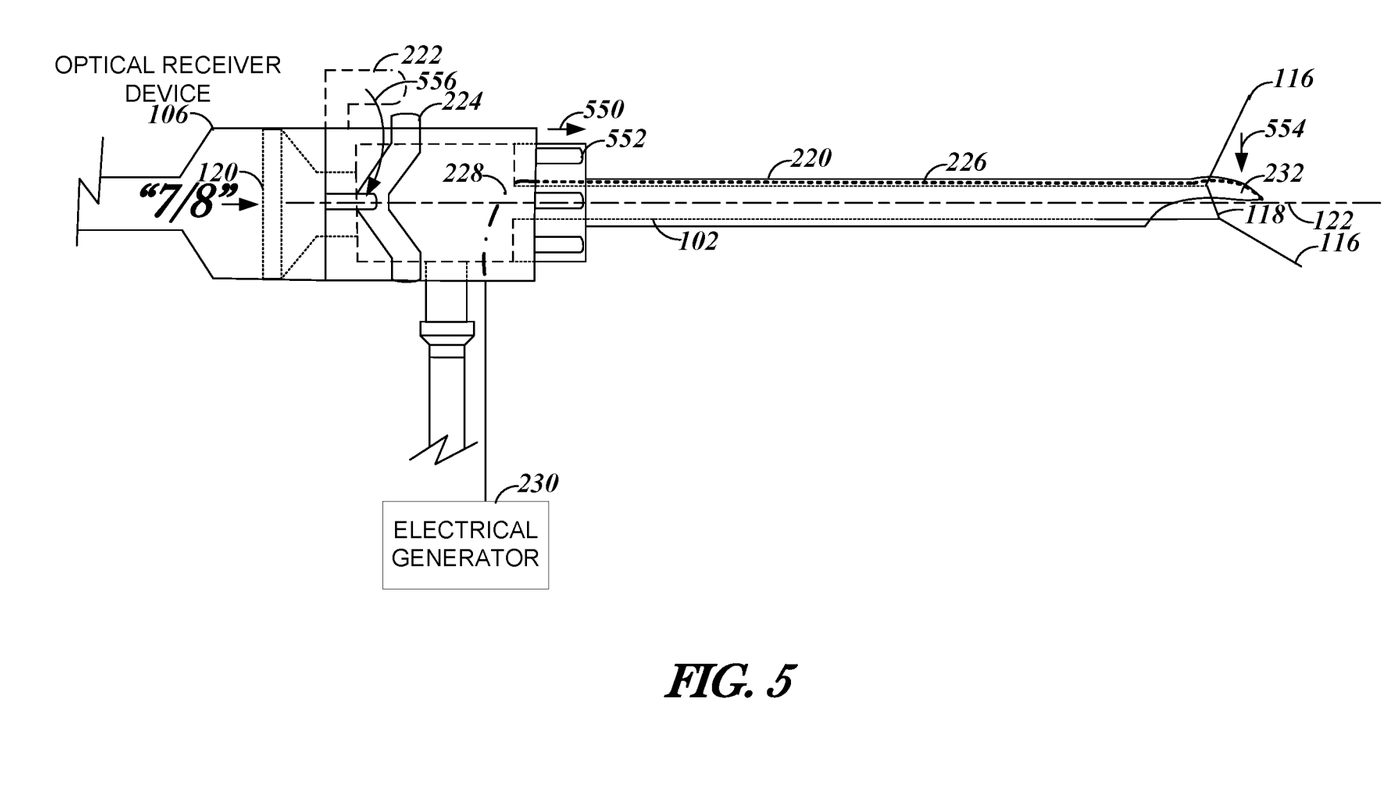
FIG. 5 illustrates an example of the endoscope system with the elongated member in an extended position.

FIG. 5 illustrates an example of the endoscope system with the elongated member 220 in an extended position. In the extended position, the elongated member 220 has moved in the direction indicated by arrow 550. In the extended position, the distal portion 232 of the elongated member 220 is bent towards the longitudinal axis 122.

A user can activate the trigger 222 to cause the elongated member 220 to translate in direction indicated by the arrow 550. In the example of FIG. 5, the user rotates the trigger 222, as indicated by arrow 556, to translate the elongated member 220 in the direction indicated by the arrow 550. As the elongated member 220 translates in the direction indicated by the arrow 550, the distal portion 232 of the elongated member 220 will eventually translate beyond the distal end 118. A shape memory of the elongated member 220 can cause the elongated member 220 to bend towards the longitudinal axis 122 of the shaft. This bending is indicated by arrow 554. The bending of the elongated member 220 can cause the elongated member 220 to be within the field of view 116. The elongated member 220 can be produced in the form illustrated in FIG. 5, such as to give it the shape memory.

Activating the trigger 222 can cause the extension device 224 to push the elongated member 220 in the direction indicated by the arrow 550. The extension device 224 can be mechanically coupled with one or more keys 552. The one or more keys 552 can help prevent rotation of the housing 234 or the extension device 224 about a perimeter of the shaft 102. The one or more keys 552 can include a spline, pin, magnet, divot, detent, clip, groove, bump, slot, or the like.

Figure 6:
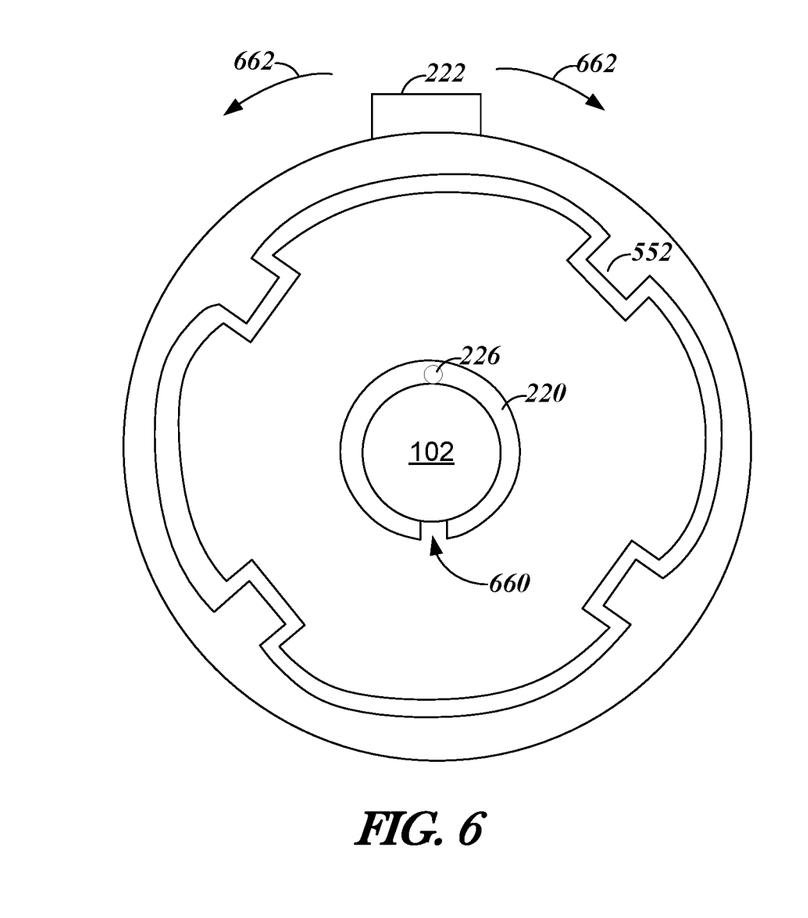
FIG. 6 illustrates an example of a portion of an endoscope system from the view indicated by the arrows labelled "6" in FIG. 2.

FIG. 6 illustrates an example of a portion of an endoscope system from the view indicated by the arrows labelled "6" in FIG. 2. The trigger 222 can be activated by rotation in multiple directions as indicated by arrows 662. The elongated member 220 can be configured to accommodate shafts 102 of varying sizes. The elongated member 220 can include a slit, gap, or other opening 660 that allows the elongated member 220 to stretch or deform to accommodate a variety of shaft sizes.

Figure 7:
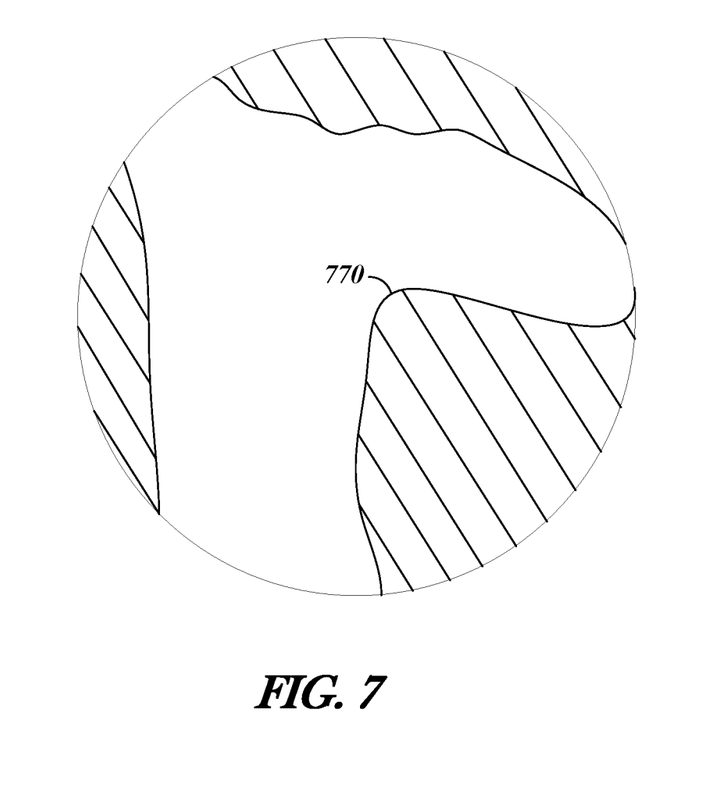
FIGS. 7 and 8 illustrate examples of a view provided by an endoscope from the view indicated by the arrow labelled "7/8" in FIG. 5.
Figure 8:
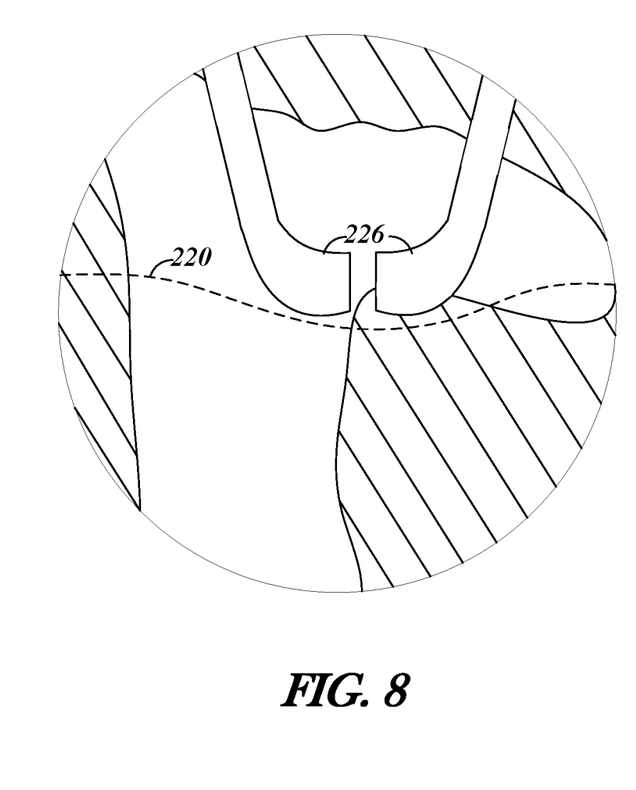

FIGS. 7 and 8 illustrate examples of a view provided by an endoscope from the view indicated by the arrow labelled "7/8" in FIG. 5. FIG. 7 illustrates a cautery target 770. The user can translate the endoscope system with the elongated member coupled thereto near the cautery target 770. The user can activate the trigger 222 to extend the elongated member 220 towards the target 770. The elongated member 220 can bend towards the longitudinal axis 122 of the shaft 102 and be in the field of view 116. FIG. 8 illustrates the elongated member 220 after activation of the trigger 222. The user can then activate another trigger to cause electrical energy to flow through the electrodes 226 and cauterize the target 770. The electrodes 226 can include or can be carried within a transparent or translucent distal portion 232. The user can retract the elongated member 220 by releasing the trigger, activating the trigger again, or activating another trigger.

Figure 9:
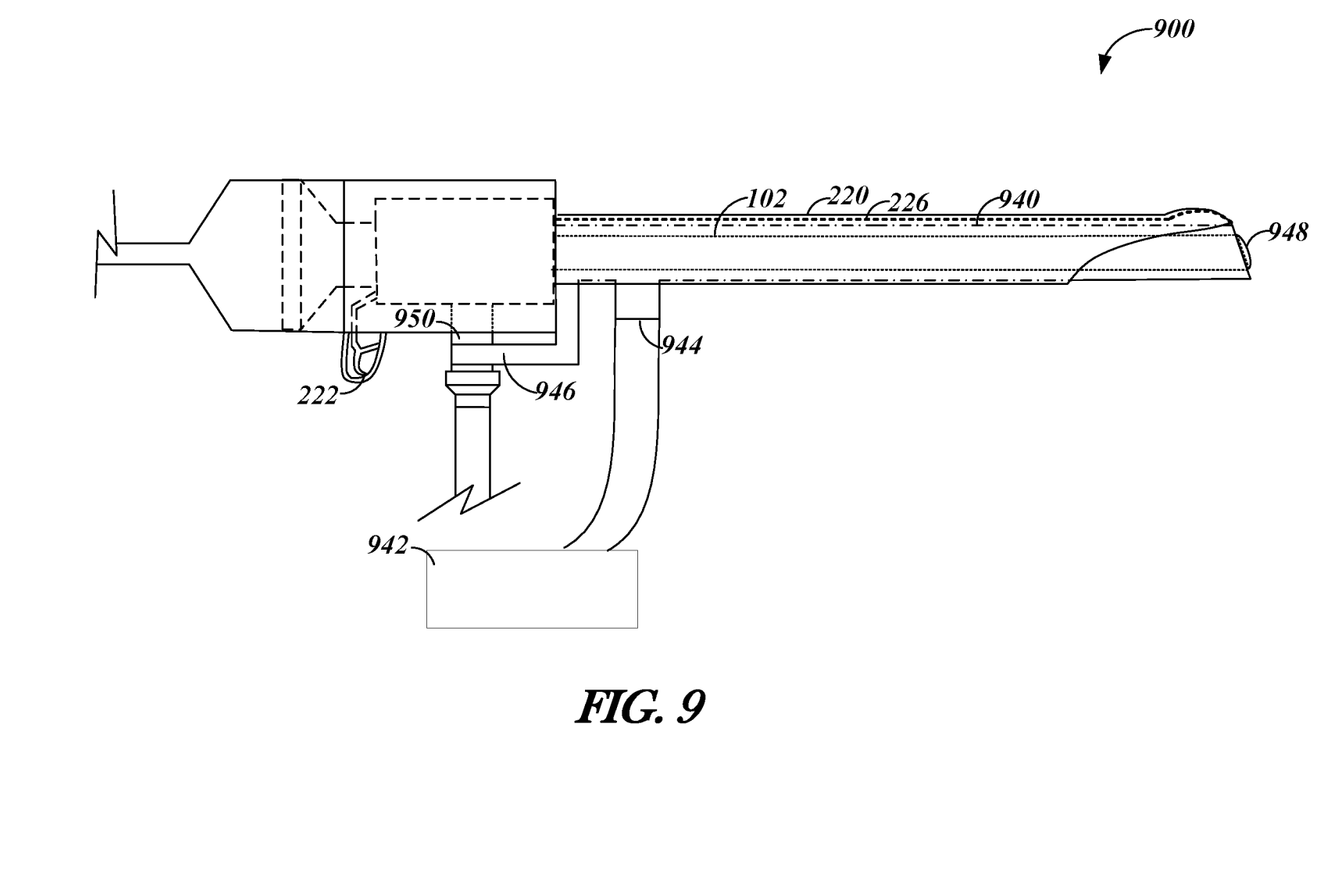
FIG. 9 illustrates an example of an endoscope system that includes an electrosurgical device mechanically coupled about a perimeter of a lens cleaning device.

FIG. 9 illustrates an example of an endoscope system 900 that includes an electrosurgical device mechanically coupled about a perimeter of a lens cleaning device 940. The electrosurgical device can be integrally formed with the lens cleaning device 940.

The lens cleaning device 940 can include a fluid portal 944. The fluid portal 944 can receive fluid from a fluid reservoir 942. The lens cleaning device 940 can direct the fluid to the distal end 118 of the endoscope. The fluid can remove debris from the distal end 118 of the endoscope 100, such as to clean the optic carrier 114, illumination carrier 112 (see FIG. 1), or a lens 948 on the distal end 118 of the endoscope. The lens 948 can alter a path of light incident thereon. From the perspective of light from the illumination carrier 112 the lens 948 can be concave and can spread the light. From the perspective of light outside the endoscope, the lens is convex and can focus the light on the optic carrier 114.

The device 940 can include a stabilizer 946 such as can help retain the device 940 in a proper orientation and position relative to the endoscope 100. The proper orientation and position is one that allows the fluid to be incident on the lens 948. The stabilizer 946 can help prevent the device 940 from rotating by a mechanically coupling to an arm 950 of the endoscope coupled to the illumination device 104. The device 940 can include an O-ring, grommet, or the like, that provides a friction or compression fit to the perimeter of the shaft 102. The O-ring, grommet, or other mechanical coupling can help prevent the device 940 from translating along the shaft 102.

The electrosurgical device can include the elongated member 220 situated around device 940. As previously discussed, the elongated member 220 can be configured to fit around shafts 102 of various dimensions. The elongated member 220 can likewise be configured to fit around the shaft 102 and the cleaning device 940. The opening 660 (see FIG. 6) is one way of configuring the elongated member 220 to accommodate the various dimensions. The dimension can be a shaft width of the shaft 102. The shaft width can be perpendicular to longitudinal axis 122.

Figure 10:
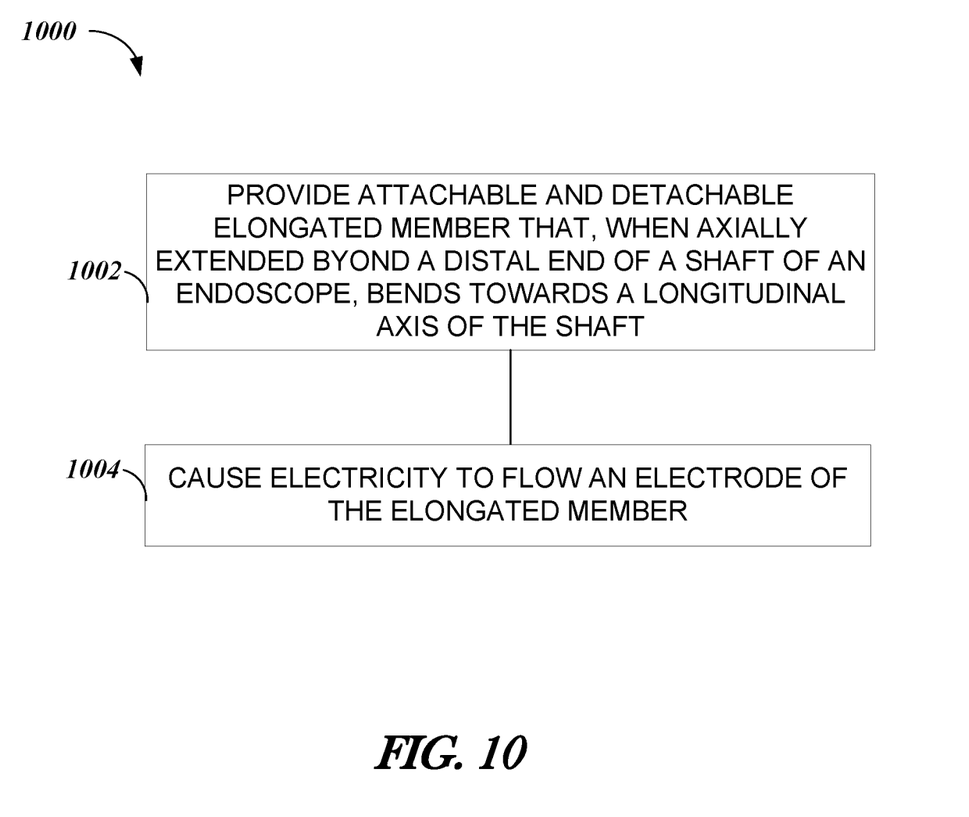
FIG. 10 illustrates an example of a method for operating an endoscope system.

FIG. 10 illustrates an example of a method 1000 for operating an endoscope system that includes an electrosurgical function. The method 1000 as illustrated includes providing an elongated member 220 that is attachable and detachable and that when axially extended beyond a distal end 118 of a shaft 102 of an endoscope 100, bends towards a longitudinal axis 122 of the shaft 102, at operation 1002; and causing electricity to flow through an electrode 226 of the elongated member 220, at operation 1004. The electrode 226 of the elongated member 220 can be exposed at a distal portion 232 of the elongated member 220.

The method 1000 can further include axially extending the elongated member 220 such that a portion of the electrode 226 extends beyond a distal end 118 of the shaft 102. The method 1000 can further include axially retracting the elongated member 220 such that a distal portion 232 of the elongated member 220 moves away from the longitudinal axis 122 of the shaft 102.

The method steps disclosed herein can be performed in any order except as specified otherwise. Moreover, one or more of the method steps can be combined with other steps; can be omitted or eliminated; can be repeated; and/or can separated into individual or additional steps.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the examples of the present invention as set forth are not intended as being exhaustive or limiting of the teachings. Further, components of the specific examples can be combined with components of other examples of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps. The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

What is claimed is:

1. An electrosurgical device comprising:
    an elongated member configured to be attached to an elongated shaft of an endoscope, the elongated member including a distal portion and at least a portion of the elongated member situated at least partially around the elongated shaft;
    an electrode exposed at the distal portion of the elongated member, the elongated member and the electrode, when axially extended beyond a distal end of the elongated shaft, bend towards a longitudinal axis of the elongated shaft; and
    an electrical interconnect coupling the electrode to an electrosurgical energy connection at a proximal portion of the elongated member.

2. The device of claim 1, wherein the electrosurgical device is an electrocautery device.

3. The device of claim 1, wherein the elongated member includes a transparent or translucent distal portion.

4. The device of claim 1, wherein the elongated member is configured to accommodate a variety of shaft widths of the elongated shaft, the elongated shaft width perpendicular to the longitudinal axis of the elongated shaft.

5. The device of claim 4, wherein the elongated member includes a gap extending from a distal portion to a proximal portion thereof to accommodate the variety of shaft widths.

6. The device of claim 1, further comprising a trigger at a proximal portion of the elongated member for actuating, by a user, an extension or retraction of the elongated member with respect to the elongated shaft.

7. The device of claim 1, wherein the elongated member is keyed to inhibit rotation of the elongated member about a longitudinal axis of the elongated member.

8. The device of claim 1, further comprising a male or female connection feature configured to mate with a female or male connection feature of the endoscope.

9. The device of claim 1, wherein the electrode is a first electrode and the electrical interconnect is a first electrical interconnect, the device further comprising:
a second electrode exposed at a distal portion of the elongated member; and
a second electrical interconnect coupling the second electrode to another electrosurgical energy connection at the proximal portion of the elongated member.

10. The device of claim 9, wherein the first and second electrodes are physically separated.

11. An electrosurgical system comprising:
an endoscope comprising:
an elongated shaft;
an optical illumination carrier to provide light to a distal end of the elongated shaft;
an optical carrier to provide light incident on the distal end of the elongated shaft to a proximal portion of the endoscope; and
an electrosurgical device comprising:
an elongated member configured to be attached to the elongated shaft, the elongated member including a distal portion and at least a portion of the elongated member situated at least partially around the elongated shaft;
an electrode on the elongated member and exposed at the distal portion of the elongated member, the elongated member and the electrode, when axially extended beyond a distal end of the elongated shaft, bend towards a longitudinal axis of the elongated shaft; and
an electrical interconnect coupling the electrode to an electrosurgical energy connection at a proximal portion of the elongated member.

12. The system of claim 11, wherein the elongated shaft is rigid compared to the distal portion of the elongated member.

13. The system of claim 11, wherein the elongated member includes a polymer material.

14. The system of claim 11, wherein the distal portion of the elongated member, when axially retracted toward a proximal end of the elongated shaft, moves away from the longitudinal axis of the elongated shaft.

15. The system of claim 11, wherein the elongated member is configured to accommodate a variety of shaft widths, the elongated shaft width perpendicular to a longitudinal axis of the elongated shaft.

16. The system of claim 15, wherein the elongated member includes a gap extending from a distal portion to a proximal portion thereof to accommodate the variety of shaft widths.

17. The system of claim 11, wherein the electrosurgical device further includes an extension feature mechanically coupled to a proximal portion of the elongated member.

18. The system of claim 17, wherein the extension feature includes a finger control and at least one of (a) a cam follower, (b) a spring, or (c) lever.

19. The system of claim 11, wherein the elongated member is keyed to inhibit rotation of the elongated member about a perimeter of the elongated shaft.

20. The system of claim 11, wherein the distal portion of the elongated member is transparent or translucent.

21. A method of operating an electrosurgical device, the method comprising:
providing an elongated member, the elongated member attachable to and detachable from an elongated shaft of an endoscope, the elongated member including an electrode exposed at a distal portion thereof and at least a portion of the elongated member situated at least partially around the elongated shaft;
axially extending the elongated member and the electrode beyond a distal end of the elongated shaft causing the elongated member and the electrode to bend toward a longitudinal axis of the elongated shaft; and
causing electricity to flow through the electrode.

22. The method of claim 21, further comprising axially extending the elongated member such that a portion of the electrode extends beyond a distal end of the elongated shaft.

23. The method of claim 21, further comprising axially retracting the elongated member such that a distal end of the elongated member moves away from the longitudinal axis of the elongated shaft.

24. An electrosurgical device comprising:
an elongated member configured to be attached to an elongated shaft of an endoscope, the elongated member including a distal portion, the elongated member configured to accommodate a variety of shaft widths of the elongated shaft, the shaft width perpendicular to a longitudinal axis of the elongated shaft;
an electrode exposed at the distal portion of the elongated member, the elongated member and the electrode, when axially extended beyond a distal end of the elongated shaft, bend towards the longitudinal axis of the elongated shaft; and
an electrical interconnect coupling the electrode to an electrosurgical energy connection at a proximal portion of the elongated member.

25. An electrosurgical system comprising:
an endoscope comprising:
an elongated shaft;
an optical illumination carrier to provide light to a distal end of the elongated shaft;
an optical carrier to provide light incident on the distal end of the elongated shaft to a proximal portion of the endoscope; and
an electrosurgical device comprising:
an elongated member configured to be attached to the elongated shaft, the elongated member including a distal portion, the elongated member configured to accommodate a variety of shaft widths of the elongated shaft, the elongated shaft width perpendicular to a longitudinal axis of the elongated shaft;
an electrode on the elongated member and exposed at the distal portion of the elongated member, the elongated member and the electrode, when axially extended beyond a distal end of the elongated shaft, bend towards the longitudinal axis of the elongated shaft; and
an electrical interconnect coupling the electrode to an electrosurgical energy connection at a proximal portion of the elongated member.

26. A method of operating an electrosurgical device, the method comprising:
providing an elongated member, the elongated member attachable to and detachable from an elongated shaft of an endoscope, the elongated member including an electrode exposed at a distal portion thereof, the elongated member configured to accommodate a variety of shaft widths of the elongated shaft, the elongated shaft width perpendicular to a longitudinal axis of the elongated shaft;
axially extending the elongated member and the electrode beyond a distal end of the elongated shaft causing the elongated member and the electrode to bend toward the longitudinal axis of the elongated shaft; and causing electricity to flow through the electrode.

\* \* \* \* \*